[19] United States Patent  
Stapp

[11] 4,100,362  
[45] Jul. 11, 1978

[54] OXIDATION PROCESS

[75] Inventor: Paul R. Stapp, Bartlesville, Okla.

[73] Assignee: Phillips Petroleum Company, Bartlesville, Okla.

[21] Appl. No.: 743,195

[22] Filed: Nov. 19, 1976

[51] Int. Cl.² .............................................. C07C 67/05
[52] U.S. Cl. ................................ 560/246; 260/343.6; 260/410.6; 260/465 D; 260/465.4; 560/183; 252/426
[58] Field of Search ............ 260/497 A, 497 R, 410.6, 260/465.4, 343.6, 465 D; 560/246, 183

[56] References Cited
U.S. PATENT DOCUMENTS

| | | | |
|---|---|---|---|
| 3,518,298 | 6/1970 | Peterson | 260/497 A |
| 3,689,535 | 9/1972 | Kollar | 260/497 R |
| 3,723,510 | 3/1973 | Ono | 260/497 R |
| 3,755,423 | 8/1973 | Onoda | 260/497 A |

FOREIGN PATENT DOCUMENTS

| | | | |
|---|---|---|---|
| 2,004,344 | 6/1971 | France. | |
| 47-39,006 | 12/1972 | Japan | 260/497 A |
| 45-31,926 | 10/1970 | Japan | 260/497 R |
| 1,138,366 | 1/1969 | United Kingdom | 260/497 A |
| 1,170,222 | 11/1969 | United Kingdom. | |

OTHER PUBLICATIONS

Morin, Ind. Eng. Chem., 43, pp. 1598–1600 (1951).
Ware, et al., J. Am. Chem. Soc., 96, pp. 7977–7981 (1974).

*Primary Examiner*—Robert Gerstl
*Assistant Examiner*—Michael Shippen

[57] ABSTRACT

The carboxylic acid esters of unsaturated alcohols, including acyloxy olefins and alkenyllactones, are prepared by the reaction of an acyclic conjugated diene, a carboxylic acid anhydride and an oxygen-containing gas in the presence of a catalytic amount of a catalyst system comprising a copper ion source, an alkali metal and a chloride or bromide ion source, wherein the carboxylic acid anhydride is both reactant and diluent, and wherein the initial reaction charge contains not more than about 1 mole of water per mole of the copper component of the catalyst system.

15 Claims, No Drawings

OXIDATION PROCESS

The present invention relates to a process for the oxidation of a conjugated diene. In one aspect the present invention relates to an improved process for preparing diacyloxy olefins. In another aspect the present invention relates to a process for preparing alkenyllactones.

Processes for the production of carboxylic acid esters of unsaturated alcohols are well known in the art. These known processes generally suffer one or more of the disadvantages that they are based on a quantitative reaction and not on a catalytic reaction, their reaction rate and yields are quite low, or separation of the reaction product is difficult.

A need exists, therefore, for a process for producing carboxylic acid esters of unsaturated alcohols by a catalytic reaction wherein the rate of reaction and yields are high and wherein the reaction product is easily separated from the reaction mixture.

Accordingly, it is an object of the present invention to provide an improved process for the production of carboxylic acid esters of unsaturated alcohols.

This and other objects, aspects and advantages of the present invention will be readily apparent from the following description and appended claims.

In accordance with the present invention there is provided a process for the preparation of an ester of a conjugated diene compound including acyloxy olefins, diacyloxy olefins and alkenyllactones, which comprises reacting (a) an acyclic conjugated diene having from 4 to 16 carbon atoms per molecule;

(b) a carboxylic acid anhydride having from 4 to 20 carbon atoms per molecule; and (c) molecular oxygen; in the presence of a catalytic amount of a catalyst system comprising copper, an alkali metal and a halide which is bromide or chloride, wherein the amount of water present in the initial reaction charge is not more than about 1 mole per mole of copper.

The term "ester" as used herein and in the claims is intended to mean open-chain esters, such as diacyloxy olefins, and cyclic esters, such as alkenyllactones.

In one embodiment of the present invention there is provided a process for producing diacyloxy olefins which comprises reacting a conjugated diene, as described above, a carboxylic acid anhydride, also described above, and molecular oxygen, in the presence of a catalyst system comprising copper and bromide ions. The product of this reaction represents an improved yield of diacyloxy olefins when no more than 1 mole of water per mole of copper is present in the initial reaction charge.

In a second embodiment of the present invention, there is provided a process for producing olefinic esters in which significant amounts of alkenyllacetones are produced in addition to diacyloxy olefins by reacting a conjugated diene, a carboxylic acid anhydride, and molecular oxygen in the presence of a catalyst system comprising copper and chloride ions. These alkenyllactones have the general formula:

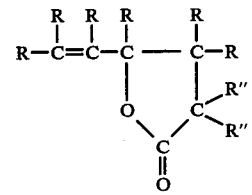

wherein R and R" are as described hereinafter.

In a third embodiment of the present invention there is provided a process for producing olefinic esters in which significant amounts of alkenyllactones are produced in addition to diacyloxy olefins by reacting a conjugated diene, a carboxylic acid anhydride and molecular oxygen in the presence of a catalyst system comprising copper and bromide ions wherein the initial reaction charge is essentially anhydrous, i.e., not more than about 0.05 moles of water per mole of the copper component.

The reaction according to the process of this invention is carried out by contacting a reaction mixture of a conjugated diene, a carboxylic acid anhydride and molecular oxygen with a catalyst system consisting essentially of a copper ion, and alkali metal ion and a chloride or bromide ion. The copper ion can initially be either cuprous or cupric. The alkali metal ion can be lithium, sodium, potassium, rubidium or cesium. Lithium is presently preferred because the lithium compounds are generally more soluble in the reaction medium than the other alkali metal compounds. It will be readily apparent that the halide ion component, i.e., the chloride or bromide ion, can be supplied, at least in part, by copper halides, alkali metal halides, or a mixture thereof, or by a separate halide source.

Any copper compound can be used that provides a source of copper ion, including such as any of the chlorides, bromides, oxides, carbonates, carboxylates having up to 18 carbon atoms per molecule, nitrates, orthophosphates, sulfates, and the like. Examples of suitable copper compounds include copper(II) acetate, copper(I) bromide, copper(II) bromide, copper(II) benzoate, copper(II) butanoate, copper(I) chloride, copper(II) chloride, copper(II) dodecanoate, copper(II) octadecanoate, copper(I) oxide, copper(II) salicylate, copper(I) carbonate, copper(I) sulfate, copper(II) sulfate, copper(II) nitrate, copper(II) orthophosphate, and the like.

Any suitable alkali metal compound can be employed as a catalyst component in the process of this invention so long as it provides a source of alkali metal ion, including such as the chlorides, bromides, oxides, hydroxides, carbonates, carboxylates, nitrates, orthophosphates, sulfates, and the like. Examples of suitable alkali metal compounds include lithium chloride, lithium bromide, lithium nitrate, lithium acetate, lithium benzoate, lithium hydroxide, lithium oxide, lithium orthophosphate, lithium octadecanoate, lithium sulfate, sodium chloride, sodium bromide, sodium acetate, sodium nitrate, sodium sulfate, potassium chloride, potassium acetate, potassium nitrate, potassium benzoate, potassium sulfate, rubidium chloride, rubidium nitrate, rubidium bromide, rubidium acetate, rubidium sulfate, cesium chloride, cesium acetate, cesium nitrate, cesium sulfate, cesium oxide, and the like.

The catalyst system of this invention can be dispersed in or upon a suitable support material such as silica, diatomaceous earth, crystalline zeolite and the like.

As noted previously, the halide ion can be supplied by the copper compound, the alkali metal compound, or both. Other halide source compounds can also be used, such as the alkaline earth metal halides, or other halides whose cation is substantially inert under the reaction conditions, or organic halides, such as dihaloolefins wherein the halogen is in an allylic position relative to the olefinic unsaturation in such haloolefins. Examples of such dihaloolefins include 1,4-dichloro-2-butene and 1,4-dibromo-2-butene and the like.

In the catalyst system of this invention, the amount of the alkali metal can range from about 0.1 to about 100 moles per mole of copper, preferably from about 1 to about 5 moles per mole of copper. The molar ratio of halide ion to copper can range from about 0.1:1 to about 100:1, preferably from about 1:1 to about 5:1.

The catalyst concentration employed according to the process of the invention can be conveniently expressed in terms of the amount of copper employed relative to the amount of the conjugated diene reactant. Broadly, the catalyst concentration can range from about 0.01 to about 1 mole of copper per mole of conjugated diene. It is presently preferred, however, to employ from about 0.1 to about 0.5 moles of copper per mole of conjugated diene.

As discussed previously, when the Cu/Br catalyst system is used to produce diacyloxy olefins, the amount of water in the reaction system must be limited to 1 mole or less of water per mole of copper. Since many of the compounds suitable for supplying the copper ion, the bromide ion, the alkali metal or combinations thereof, contain water of hydration, it is necessary, in some cases, to reduce the water of hydration to the desired level. The desired water concentration can be achieved most simply by proper choice of the compounds supplying the desired catalyst components. Alternatively, the catalyst-supplying compounds can be dehydrated as follows:

1. The catalyst components are admixed with the carboxylic acid anhydride which will be later used to provide the acyloxy moiety of the desired diacyloxy olefin.
2. The mixture is heated, preferably with stirring, to an elevated temperature for a suitable time. Generally, a temperature of at least about 120° C for at least about 2 hours should be sufficient.
3. The mixture is then cooled and evaporated to dryness under reduced pressure. The dehydration step can be repeated as necessary to provide the desired amount of water in the reaction system.

When the Cu/Br catalyst system is used to produce alkenyllactones, it may be necessary to carry out the above dehydration step several times in order to assure complete dryness of the catalyst system.

When the Cu/Cl catalyst system is used to produce alkenyllactones, the amount of water present in the reaction system is not so critical as with the Cu/Br catalyst system. It is, however, desirable to limit the concentration of water in the reaction system to about 1 mole or less of water per mole of copper. Thus, when using catalyst-supplying compounds having more than 1 mole of water of hydration per mole of catalyst component, it may be necessary to carry out the above dehydration step.

The acyclic conjugated dienes employed in the process of the present invention have the general formula

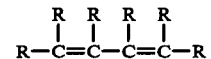

wherein each R is selected from the group consisting of —H, —F, —Cl, —Br, —I, —CN, —COOR', monovalent hydrocarbyl radical having up to 12 carbon atoms including alkyl, cycloalkyl and aryl; and combination radicals including alkaryl, aralkyl, cycloalkylaryl, and the like, and R' is —H or an alkyl or aryl radical having up to 10 carbon atoms.

The acyclic conjugated dienes employed in the process of this invention contain from 4 to 16, preferably 4 to 8, carbon atoms per molecule. It is presently preferred that these dienes contain only carbon and hydrogen, although a variety of substituents can be present in the conjugated dienes which are unreactive under the reaction conditions utilized and thus do not interfere with the desired reaction.

Examples of suitable acyclic conjugated dienes include: 1,3-butadiene, 2-methyl-1,3-butadiene, 2-chloro-1,3-butadiene, 2-ethyl-1,3-butadiene, 2-chloro-3-methyl-1,3-butadiene, 1,4-diphenyl-1,3-butadiene, 1,3-hexadiene, 1,3-pentadiene, 1,3-octadiene, 2-cyano-1,3-butadiene, 2-cyclohexyl-1,3-butadiene, 2-methylene-3-butenoic acid, and 2,4-pentadienenitrile. Particularly preferred are 1,3-butadiene and isoprene because of availability and reactivity of these compounds.

The carboxylic acid anhydrides employed in the process of the present invention have the general formula

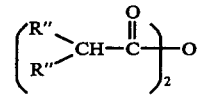

wherein each R" is individually selected from the group consisting of hydrogen and alkyl having 1 to 8 carbon atoms.

The carboxylic acid anhydride is utilized both as a reactant and as a diluent in the process of this invention. Accordingly, the amount of carboxylic acid anhydride employed in the process of this invention should be at least equimolar to the amount of conjugated diene charged to the reaction system, while the upper limit of the amount of carboxylic acid anhydride is restricted only by reasonable constraints on separation methods for the reaction mixture. It is convenient to employ about 1 liter of the carboxylic acid anhydride per mole of the conjugated diene reactant.

Examples of suitable carboxylic acid anhydrides include: acetic anhydride, propanoic anhydride, butanoic anhydride, pentanoic anhydride, hexanoic anhydride, octanoic anhydride, decanoic anhydride, bis(2-ethylhexanoic) anhydride, bis(2-octanoic) anhydride, bis(2-methylpropanoic) anhydride, bis(3-methylbutanoic) anhydride, and the like.

The process of the present invention can be carried out in the gas phase or the liquid phase. It is presently preferred to carry out the process in the liquid phase with the reactants and the catalyst components in the liquid phase, with the exception of oxygen which is a reactant, since milder conditions such as lower temperatures and pressures can be utilized which tend to reduce the amount of by-products.

The amount of oxygen provided to the reaction is not believed to be critical although it is recognized that an undesirably slow reaction will result if the concentration of oxygen is too low. It should also be recognized that explosive conditions could be achieved if the amount of oxygen added to the reaction system is not controlled. The reaction of this invention, as is generally true of oxidation reactions, appears to be highly exothermic, thus indicating caution in adding oxygen to the system. It is therefore desirable to add the oxygen incrementally or continuously during the reaction to avoid an explosive range of oxygen concentration and to allow control of the reaction temperature. A reaction vessel having efficient mixing means is also desirable to avoid build-up of dangerous concentrations of free oxygen.

The reaction is carried out under an oxygen pressure ranging from 0.1 to 1000, preferably 5 to 200, psig of oxygen above the autogenous pressure obtained at the temperature employed.

Essentially pure oxygen can be employed as well as mixtures of oxygen with inert gases. Air can also be used as the source of free oxygen.

The process of this invention can be carried out in the range of 25° to 200° C, preferably about 70° to 150° C.

The reaction time employed in the process of this invention is not critical and can vary widely, depending generally on the desired degree of conversion of the starting conjugated diene. The reaction time in a batch type process can vary between 1 hour or less to 18 hours or more.

It is also within the scope of this invention to carry out the process of this invention in a continuous fashion, either in the vapor phase or in the liquid phase. In a continuous process, it is desirable to utilize a supported catalyst, as described previously.

The reaction mixtures obtained according to the process of this invention are generally vented to remove any unreacted oxygen and conjugated diene and then distilled to remove any carboxylic acid anhydride or carboxylic acid which may be present. The product mixture remaining is usually fractionally distilled to recover one or more fractions containing the diacyloxy olefins. The diacyloxy olefins which are recovered from the product mixture include, in many instances, an amount of 1,2-isomer, which can be recycled to the reaction zone for conversion to the more desired 1,4-diacyloxy olefin. The above mentioned 1,4-diacyloxy olefins have utility as intermediates for the preparation of the corresponding saturated diols, such as for example, 1,4-butanediol. In addition, British Pat. No. 1,170,222 describes the preparation of tetrahydrofurans, starting with conjugated dienes and proceeding through the 1,4-diacyloxybutenes. Tetrahydrofuran itself, of course, would be produced starting with 1,3-butadiene. The above mentioned saturated diols, such as 1,4-butanediol and tetrahydrofurans especially tetrahydrofuran itself, have obvious utility in the chemical arts.

The lactones which may be prepared according to the process of the instant invention are useful as solvents, particularly as solvents for polymers and due to their activity, as chemical intermediates especially for the preparation of polymers from polyamines or acrylates. These lactones which may be produced according to the instant invention can be separated from the product reaction mixture in essentially the same manner as that described above for the dicayloxy olefins, such as by fractional distillation.

The following examples further illustrate the invention:

EXAMPLE I

A series of runs was carried out utilizing 1,3-butadiene as the acyclic conjugated diene reactant with a catalyst system of cupric acetate monohydrate (48 mmoles), lithium bromide (75 mmoles), and 1,4-dibromo-2-butene (21.5 mmoles). Each of these runs was conducted utilizing a 250 ml Fisher-Porter aerosol compatibility bottle equipped with a magnetic stirrer as the reactor means. In each of the runs, the reactor was charged with the catalyst system described above and the indicated amount of reaction/diluent followed by the addition of 1,3-butadiene to the reactor in the vapor phase. The reactor was then placed in an oil bath, pressured to 30 psig with oxygen and heated to 140° C over a period of about 1 hour. The reaction was continued at 140° C for about 5-6 hours during which time at about 10 to 30 minute intervals the reactor was repressured to 120 psig with oxygen. At the conclusion of each reaction period, the reactor was vented and the reaction mixture processed in the following manner. In run no. 1, the reaction mixture was transferred using acetic acid to a distillation flask and then distilled in an 18 inch Vigreux column to obtain two fractions. Fraction no. 2 which boiled over a range of 60°-112° C at 8 mm mercury pressure weighed 32.5 grams. This fraction was analyzed by gas-liquid phase chromatography (GLC). Fraction no. 1 which boiled over a range of 53°-70° C at 70 mm mercury pressure weighed 98.0 grams and was determined by GLC analysis to be 33% acetic anhydride and 67% acetic acid. In runs 2 and 3, the reaction mixture, after cooling and venting of the reactor, was filtered to remove solids and the filtrate then transferred to a distillation flask from which essentially all the acetic acid and acetic anhydride was distilled away. The residue was then extracted with a diethyl ether/water mixture and the aqueous layer extracted with additional diethyl ether. The combined diethyl ether extracts were washed with water, sodium carbonate, then dried over anhydrous magnesium sulfate and filtered. The diethyl ether was removed from the filtrate by evaporation to give a brown oil which was distilled away from a small amount of high boiling residue. The volatile material was analyzed by gas-liquid phase chromatography. The amount of 1,3-butadiene utilized in each run and the reactant/diluent system employed as well as the results in each of the three runs are presented below in Table I.

Table I

| Run No. | Acetic Acid, ml | Acetic Anhydride, ml | 1,3-Butadiene mmole | Diacetoxybutene % Yield[a] | Isomer Distribution, % | | |
|---|---|---|---|---|---|---|---|
| | | | | | 1,2- | cis-1,4- | trans-1,4- |
| 1 | 0 | 75 | 218.5 | 75.3 | 30 | 7 | 63 |
| 2 | 50 | 25 | 213.0 | 68.5 | 32 | 68[b] | |
| 3 | 50 | 25 | 203.7 | 70.2 | 17 | 7 | 76 |

[a]Yield of combined diacetoxybutene isomers based on 1,3-butadiene charged.
[b]Value for cis- and trans- isomer content not individually determined in this run.

The results shown in Table I above demonstrate that with the copper/lithium/bromide ion catalyst system in the presence of 1 mole of water per mole of copper that the use of acetic anhydride as the sole reactant/diluent gives an improved yield of the desired diacetoxybutenes compared to the use of a mixture of acetic acid and acetic anhydride as the reactant/diluent system. It can also be noted that runs 2 and 3 were duplicate runs.

EXAMPLE II

A series of runs were conducted in which the effect of acetic anhydride versus a mixture of acetic acid and acetic anhydride as the reactant/diluent system for two known catalyst systems for the oxidation of butadiene to diacetoxybutenes was examined. Two of the runs (4 and 5) employed selenium dioxide ($SeO_2$) (20 mmoles), lithium bromide (75 mmoles), and 1,4-dibromo-2-butene (10.7 or 21.5 mmoles, respectively). Runs 6 and 7 utilized a catalyst system of antimony oxide ($Sb_2O_3$) 24 or 10 mmoles, respectively), lithium bromide (75 mmoles) and 1,4-dibromo-2-butene (21.5 mmoles). The runs of this example were conducted in essentially the same manner as that described above for the runs of Example I and the product mixtures were worked up in essentially the same manner as that described for run no. 1 of Example I. The amounts of butadiene employed in the runs of the instant example as well as the results obtained in said runs are presented below in Table II.

Table II

| Run No. | Acetic Acid, ml | Acetic Anhydride, ml | 1,3-Butadiene mmole | Diacetoxybutene % Yield$^{(a)}$ | Isomer Distribution, % | | |
|---|---|---|---|---|---|---|---|
| | | | | | 1,2- | cis-1,4- | trans-1,4- |
| 4 | 0 | 75 | 222.2 | 30.9 | 15 | 14 | 71 |
| 5 | 50 | 25 | 198.1 | 83.4 | 21 | 14 | 65 |
| 6 | 0 | 75 | 212.9 | 62.9 | 23 | 12 | 65 |
| 7 | 50 | 25 | 205.5 | 75.0 | 36 | 16 | 48 |

The results shown for runs 4 through 7 of TAble II above demonstrates that with known catalyst systems for the oxidation of butadiene to diacetoxybutenes the use of acetic anhydride alone as a reaction/diluent actually produces significantly lower yields of the diacetoxybutenes compared to a mixture of acetic acid and acetic anhydride as the reactant/diluent system. These results are in contrast to that obtained in the instant invention and demonstrated in the results of Table I above.

EXAMPLE III

A run was carried out according to the instant invention utilizing bromide ion as the halide ion component of the catalyst system but under essentially anhydrous conditions and with acetic anhydride alone as the reactant/diluent system for the run. In this run (no. 8), a 250 ml Fisher-Porter aerosol compatibility bottle equipped with a magnetic stirrer was charged with 6.5 grams (75 mmoles) of lithium bromide, 9.6 grams (48 mmoles) of cupric acetate monohydrate and 75 ml of acetic anhydrie. The bottle was heated at 140° C for 2 hours, cooled and evaporated to dryness under reduced pressure. A second dehydration step was conducted using 150 ml of acetic anhydride in the same manner as that just described.

At the end of this treatment the inorganic salts were white. The reactor was then charged with 2.5 grams (10.7 mmoles) of 1,4-dibromo-2-butene in 75 ml of acetic anhydride. 1,3-Butadiene, 11.3 grams (209.2 mmoles) was then charged to the vapor phase and the reactor was allowed to stand overnight. The reactor bottle was placed in an oil bath, pressured to 30 psig with oxygen and heated to 140° C. About 1.5 hours was required to reach the desired reaction temperature of 140° C and the reaction continued for about 7.5 hours with intermittent pressuring of the reactor to 120 psig with oxygen at about 20–40 minute intervals. The reactor was cooled, vented and the reaction mixture transferred to a distillation flask with the aid of 22 grams of acetic anhydride. The reaction mixture was distilled through an 18 inch Vigreux column and two fractions were collected. Fraction 1 which boiled from 56° to 66° C at 50 mm mercury pressure weighed 113.9 grams and fraction 2 which boiled at 55° to 118° C at 5 mm mercury pressure weighed 22.7 grams. GLC analysis of fraction 1 indicated a composition of 80.3% acetic anhydride and 19.7% acetic acid. Analysis of fraction 2 indicated 3.8 grams acetic anhydride, 6.34 grams (56.6 mmoles) of 4-vinyl-4-butyrolactone, 4.67 grams (27.1 mmoles) of 1,2-diacetoxy-3-butene, 0.79 grams (4.6 mmoles) of cis-1,4-diacetoxy-2-butene and 6.45 grams (37.5 mmoles) of trans-1,4-diacetoxy-2-butene. The yield of diacetoxybutenes was 33.1% based on butadiene charged while the yield of the 4-vinyl-4-butyrolactone was 27.1% based on the butadiene charged. These results are also strikingly different from those achieved in run 1 of Example I above wherein a cupric acetate monohydrate was employed as the copper component of the catalyst system. These results indicate that under essentially anhydrous conditions the copper/lithium/bromide ion catalyst system in acetic anhydride as the reactant/diluent can give significant amounts of the alkenyllactone in addition to the diacetoxybutenes.

EXAMPLE IV

As another control run a catalyst system outside of the instant invention was utilized to carry out the oxidation of 1,3-butadiene in the presence of acetic anhydride alone as the reactant/diluent. The catalyst system of this run (no. 9) was manganese acetate tetrahydrate - 7.5 grams (30 mmoles) and lithium bromide - 6.5 grams (75 mmoles). This catalyst system was treated in the manner described for the catalyst of run no. 8 of Example III above. A 250 ml Fisher-Porter aerosol compatibility bottle equipped with a magnetic stirrer was charged with the above catalyst and 100 ml of acetic anhydride. The bottle was sealed and heated at 140° C for 2 hours then the acetic acid and acetic anhydride were removed on a water aspirator. A similar second treatment with 100 ml of acetic anhydride followed by evaporation was carried out to insure dryness of the catalyst. The bottle reactor was then charged with 4.6 grams (21.5 mmoles) of 1,4-dibromo-2-butene in 75 ml of acetic anhydride followed by 11.4 grams (211.1 mmoles) of butadiene charged to the reactor in the vapor phase. The bottle reactor was placed in an oil bath, pressurized to 30 psig with oxygen and heated to 140° C. About 1 hour was required to reach the desired reaction temperature of 140° C after which the reaction was continued for about 5.25 hours. During the reaction period the reactor was pressured intermittently to about 130 psig with oxygen at about 20–40 minute intervals. At the end of the reaction period the reactor was cooled, vented and the mixture transferred to a distillation flask and then distilled through an 18 inch Vigreux column. Two fractions were collected with fraction 1 which boiled at 50° to 68° C at 50 mm pressure weighing 90.8 grams while fraction 2 which boiled at 54° to 105° C at 5 mm mercury pressure weighed 22.0 grams. GLC analysis of fraction 1 indicated the composition to be 67.9% acetic anhydride and 32.1% acetic acid. Analysis of fraction 2 by GLC indicated the presence of 3.71 grams (21.6 mmoles) of 1,2-diacetoxy-3-butene, 2.03 grams (11.8 mmoles) of cis-1,4-di-acetoxy-2-butene and 8.45 grams (49.1 mmoles) of trans-1,4-diacetoxy-2-butene. Only traces of 4-vinyl-4-butyrolactone were present in the reaction mixture. The yield of diacetoxybutenes thus obtained based on the butadiene charged was 39.1%. Comparison of the results of run 9 with those of run 8 of Example III indicate that the manganese-based catalyst responded very differently to the exhaustive removal of water as compared to the similar treatment of the copper-based catalyst system of the instant invention.

EXAMPLE V

A run was conducted in which acetic anhydride alone was utilized as the reactant/diluent for the oxidation of 1,3-butadiene with a catalyst system of the instant invention wherein the halide component was chloride rather than bromide as in Example I above. The catalyst system in this run (run no. 10) was cupric acetate monohydrate - 9.6 grams (48 mmoles), 1,4-dichloro-2-butene-2.8 grams (22.5 mmoles, and lithium chloride - 3.2 grams (75.3 mmoles). The above catalyst system was charged to a 250 ml Fisher-Porter aerosol compatibility bottle equipped with a magnetic stirrer and which contained 75 ml of acetic anhydride. To this mixture, 12.0 grams (222.2 mmoles) of 1,3-butadiene was charged to the vapor phase. The reactor bottle was placed in an oil bath, pressured to 30 psig with oxygen and heated to 140° C. About 1 hour was required to reach the desired 140° C reaction temperature and the reaction was continued then for 6 hours with intermittent pressuring of the reactor to 120 psig with oxygen at 10–40 minute intervals. The reactor was cooled, vented and the reaction mixture transferred to a distillation flask using 30 grams of acetic anhydride to wash the mixture from the reactor. The mixture was distilled through an 18 inch Vigreux column and two fractions were collected. Fraction 1 boiling from 45°–66° C at 50 mm mercury pressure weighed 103.0 grams while fraction 2 boiling from 58°–118° C at 5 mm pressure weighed 24.9 grams. GLC analysis of fraction 1 demonstrated that it was composed of 71% acetic anhydride, and 29% acetic acid. GLC analysis of fraction 2 indicated the presence of 3.48 grams (20.3 grams) of 1,2-diacetoxy-3-butene and 6.67 grams (38.9 mmoles) of trans-1,4-diacetoxy-2-butene for a yield of 26.6% of diacetoxybutenes based on the butadiene charged. In addition, the reaction mixture contained 11.42 grams (102.0 mmoles) of 4-vinyl-4-butyrolactone which represents a yield of 45.9% of the lactone based on the butadiene charged. This result is then a striking contrast to that shown for run no. 1 of Example I but which employed the bromide as the halogen component of the catalyst system rather than chloride as in the instant run.

EXAMPLE VI

Other runs were carried out which serve as control runs for invention run 10 of Example V above. Each of the runs of the instant example were carried out in the same type of apparatus as previously employed, i.e., a 200 ml Fisher-Porter aerosol compatibility bottle equipped with magnetic stirrer. The catalyst system in each of the runs was composed of cupric acetate monohydrate, lithium chloride, and 1,4-dichloro-2-butene. The reactant/diluent utilized in each of the runs was 50 ml of glacial acetic acid and 25 ml of acetic anhydride. Each run also utilized 1,3-butadiene as the acyclic conjugated diene reactant. Essentially the same procedure as previously employed was utilized in this series of runs for charging of the catalyst system ingredients, reactant/diluent, and butadiene to the reactor. Essentially the same procedure in this series of runs was also utilized in raising the reaction temperature to the desired level and maintaining oxygen in the reaction system by intermittent repressuring at 10–40 minute intervals. The reaction mixtures were worked up by either extraction directly into diethyl ether or by utilization of a water/diethyl ether mixture with additional diethyl ether extraction of the aqueous phase followed by removal of the diethyl ether by distillation and finally fractional distillation of the residue after diethyl ether removal. In one instance (run 11) the acetic acid/acetic anhydride was removed from the reaction mixture by distillation prior to extraction of the residual reaction mixture with the water/diethyl ether mixture. In any event, analyses of the fractions from the distillation were carried out by gas-liquid phase chromatography as in the previous examples. The amounts of catalyst system ingredients, butadiene and other reaction conditions utilized in this series of runs are presented below in Table III while the results of said runs are presented in Table IV.

Table III

| Run No. | Cu mmole | LiCl mmole | 1,4-DCB[a] mmole | 1,3-Bd[b] mmole | Temp. °C | Time[c] hours | $O_2$,[d] psig |
|---|---|---|---|---|---|---|---|
| 11 | 48.0 | 75.3 | 22.5 | 179.6 | 120 | 4.5 | 100 |
| 12 | 48.0 | 75.3 | 22.5 | 203.7 | 140 | 4.5 | 110 |
| 13 | 48.0 | 75.3 | 22.5 | 231.6 | 140 | 5 | 120 |
| 14 | 12.0 | 75.3 | 5.6 | 198.2 | 140 | 5.75 | 120 |

[a]1,4-DCB = 1,4-dichloro-2-butene.
[b]1,3-Bd = 1,3-butadiene.
[c]Includes time required to reach reaction temperature.
[d]Repressure value during reaction period.

Table IV

| Run No. | 1,2-DAB[a] mmole | c-1,4-DAB[b] mmole | t-1,4-DAB[c] mmole | % Yield[d] DAB | VBL[e] mmole | % Yield[d] VBL |
|---|---|---|---|---|---|---|
| 11[f] | 39.4 | 1.8 | 48.7 | 50 | 15.1 | 8.4 |
| 12 | 36.2 | —[g] | 66.7 | 53 | 8.1 | 4 |
| 13 | 26.2 | 2.1 | 21.9 | 22 | 9.8 | 4 |

Table IV-continued

| Run No. | 1,2-DAB[a] mmole | c-1,4-DAB[b] mmole | t-1,4-DAB[c] mmole | % Yield[d] DAB | VBL[e] mmole | % Yield[d] VBL |
|---|---|---|---|---|---|---|
| 14 | 22.6 | —[g] | 20.5 | 22 | 10.7 | 5.4 |

[a]1,2-DAB = 1,2-diacetoxy-3-butene.
[b]c-1,4-DAB = cis-1,4-diacetoxy-2-butene.
[c]t-1,4-DAB = trans-1,4-diacetoxy-2-butene.
[d]Yield based on 1,3-butadiene charged.
[e]VBL = 4-vinyl-4-butyrolactone.
[f]GLC also showed 4.8 mmole of 1-acetoxy-4-chloro-2-butene present in the product mixture.
[g]Not detected in measurable amounts by GLC.

GLC analysis also indicated the presence of a small amount (about 1 gram) of unidentified material in the reaction mixture from each of the above runs.

It will be apparent that runs 12 and 13 of the instant example represent runs which are closely analogous to the invention run 10 of Example V above. The essential difference between runs 10, 12 and 13 being the utilization of acetic anhydride alone as the reactant/diluent in the invention run whereas the runs of this example utilized in each instance a mixture of acetic acid and acetic anhydride as the reactant/diluent system. Although the yield of diacetoxybutenes in run 13 was for some unknown reason significantly lower than that obtained in run 12, the results of these runs demonstrate that the yield of 4-vinyl-4-butyrolacetone is much lower when a reactant/diluent system of acetic acid and acetic anhydride is employed in contrast to the invention run (no. 10) which utilized acetic anhydride alone as the reactant/diluent system.

Reasonable variations and modifications, which will be apparent to those skilled in the art, can be made in this invention without departing from the spirit and scope thereof.

What is claimed is:

1. A process for the production of unsaturated esters from a conjugated diene which comprises reacting
    (a) an acyclic conjugated diolefin having from 4 to 16 carbon atoms per molecule of the formula

wherein each R is individually selected from the group consisting of —H, —F, —Cl, —Br, —I, —CN, —COOR′, alkyl having from 1 to 12 carbon atoms, cycloalkyl having from 5 to 12 carbon atoms and aryl having from 6 to 12 carbon atoms, and combinations thereof, and said R′ is selected from the group consisting of —H, alkyl having from 1 to 10 carbon atoms and aryl having from 6 to 10 carbon atoms;
    (b) a carboxylic acid anhydride having from 4 to 20 carbon atoms per molecule of the formula

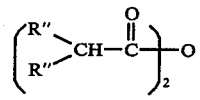

wherein each R″ is individually selected from the group consisting of hydrogen and alkyl having from 1 to 8 carbon atoms; and
    (c) molecular oxygen; in the presence of a catalyst system consisting essentially of cuprous acetate, lithium bromide and 1,2-dibromo-2-butene wherein the amount of copper ion is in the range of from 0.01 to about 1 mole of copper ion per mole of said conjugated diene, the amount of lithium metal ion is in the range of from 0.1 to about 100 moles per mole of copper ion, and the amount of bromide ion is in the range of from 0.1 to about 100 moles per mole of copper ion, and wherein the reaction is carried out in a reaction system wherein the total amount of water present in the initial reaction charge is not greater than about 1 mole of water per mole of copper ion.

2. The process of claim 1 wherein the amount of copper ion is in the range of from about 0.1 to about 0.5 mole per mole of said conjugated diene.

3. The process of claim 1 wherein the amount of lithium metal ion is in the range of from about 1 to about 5 moles per mole of copper ion.

4. The process of claim 1 wherein the amount of bromide ion is in the range of from about 1 to about 5 moles per mole of copper ion.

5. The process of claim 1 wherein said acyclic conjugated diene is a hydrocarbon containing only carbon and hydrogen.

6. The process of claim 1 wherein said acyclic conjugated diene has from 4 to 8 carbon atoms per molecule.

7. The process of claim 1 wherein said acyclic conjugated diene is 1,3-butadiene.

8. The process of claim 1 wherein said carboxylic acid anhydride is acetic anhydride.

9. The process of claim 1 wherein the amount of said carboxylic acid anhydride is at least equimolar to the amount of said conjugated diene charged.

10. The process of claim 1 wherein the amount of water present in the initial charge is in the range of from about 0.05 to about 1 mole per mole of copper ion.

11. The process of claim 10 wherein said carboxylic acid anhydride is acetic anhydride, and the initial reaction charge is essentially anhydrous.

12. The process of claim 10 wherein the amount of water in the initial charge is about 1 mole per mole of copper ion.

13. The process of claim 1 wherein said reaction is carried out at a temperature in the range of 25° to 200° C.

14. The process of claim 1 wherein said reaction is carried out at an oxygen pressure of 0.1 to 1000 psig above autogenous pressure.

15. The process of claim 1 wherein said reaction is carried out in the liquid phase.

* * * * *